US009668977B2

(12) United States Patent
Schattka et al.

(10) Patent No.: US 9,668,977 B2
(45) Date of Patent: Jun. 6, 2017

(54) COATING COMPOSITION SUITABLE FOR PHARMACEUTICAL OR NUTRACEUTICAL DOSAGE FORMS

(75) Inventors: Jan Hendrik Schattka, Darmstadt (DE); Christian Meier, Darmstadt (DE); Florian Hermes, Frankfurt (DE)

(73) Assignee: Evonik Röhm GmbH, Darmstadt (DE)

( * ) Notice: Subject to any disclaimer, the term of this patent is extended or adjusted under 35 U.S.C. 154(b) by 471 days.

(21) Appl. No.: 14/115,632

(22) PCT Filed: Jun. 17, 2011

(86) PCT No.: PCT/EP2011/060097
§ 371 (c)(1),
(2), (4) Date: Nov. 5, 2013

(87) PCT Pub. No.: WO2012/171576
PCT Pub. Date: Dec. 20, 2012

(65) Prior Publication Data
US 2014/0079792 A1 Mar. 20, 2014

(51) Int. Cl.
| | |
|---|---|
| A61K 9/16 | (2006.01) |
| A61K 9/50 | (2006.01) |
| C08F 2/22 | (2006.01) |
| A61K 9/20 | (2006.01) |
| C08F 265/06 | (2006.01) |
| A61K 31/522 | (2006.01) |

(52) U.S. Cl.
CPC .......... *A61K 9/5026* (2013.01); *A61K 9/1635* (2013.01); *A61K 9/2027* (2013.01); *A61K 9/5089* (2013.01); *A61K 31/522* (2013.01); *C08F 2/22* (2013.01); *C08F 265/06* (2013.01); *C08L 2207/53* (2013.01)

(58) Field of Classification Search
None
See application file for complete search history.

(56) References Cited

U.S. PATENT DOCUMENTS

| | | | |
|---|---|---|---|
| 4,876,313 A | 10/1989 | Lorah | |
| 5,705,189 A | 1/1998 | Lehmann et al. | |
| 6,143,326 A | 11/2000 | Möckel et al. | |
| 6,777,489 B1 | 8/2004 | Carey et al. | |
| 2007/0179240 A1 | 8/2007 | Chalmers et al. | |
| 2007/0225442 A1 | 9/2007 | Ootuka et al. | |
| 2008/0014257 A1* | 1/2008 | He | A61K 9/2009 424/457 |
| 2008/0020041 A1* | 1/2008 | Ayres | A61K 9/5078 424/472 |
| 2008/0058473 A1 | 3/2008 | Freidzon et al. | |
| 2008/0166416 A1* | 7/2008 | Lizio | A61K 9/5026 424/494 |
| 2010/0221324 A1 | 9/2010 | Petereit et al. | |
| 2013/0115185 A1* | 5/2013 | Tamareselvy | A61K 8/025 424/70.16 |

FOREIGN PATENT DOCUMENTS

| | | | |
|---|---|---|---|
| CN | 101801356 A | 8/2010 | |
| DE | WO 2010034342 A1 * | 4/2010 | .......... A61K 9/5078 |
| EP | 0 704 207 A2 | 4/1996 | |
| EP | 1 008 635 | 6/2000 | |
| EP | 1 754 766 | 2/2007 | |
| RU | 2 193 881 C2 | 12/2002 | |
| RU | 2 359 985 C1 | 6/2009 | |
| RU | 2 403 015 C2 | 11/2010 | |
| WO | 01 05844 | 1/2001 | |
| WO | 2005 010065 | 2/2005 | |
| WO | WO 2005/079760 A1 | 9/2005 | |
| WO | WO 2006/094737 A2 | 9/2006 | |
| WO | WO 2006/132471 A1 | 12/2006 | |
| WO | 2008 028062 | 3/2008 | |
| WO | 2009 036811 | 3/2009 | |
| WO | WO 2012006402 A1 * | 1/2012 | ............. A61K 8/025 |

OTHER PUBLICATIONS

Y Zu, Y Luo, Su Ahmed. "Effect of Neutralization of Poly(Methacrylic Acid-co-ethyl Acrylate) on Drug Release From Enteric-coated Pellets Upon Accelerated Storage." Drug Development and Industrial Pharmacy, vol. 33, 2007, pp. 457-473.*
Combined Chinese Office Action and Search Report issued Feb. 25, 2015 in Patent Application No. 201180070617.5 (with English language translation).
Lakhya J. Borthakur, et al., "Preparation of core-shell latex particles by emulsion co-polymerization of styrene and butyl acrylate, and evaluation of their pigment properties in emulsion paints" J. Coat. Technol. Res., vol. 7, No. 6, 2010, pp. 765-772.
Office Action issued Oct. 27, 2015 in Russian Patent Application No. 2014101228/15 (001654) (with English language translation).
U.S. Appl. No. 14/118,078, filed Nov. 15, 2013, Nollenberger, et al.
U.S. Appl. No. 14/114,752, filed Oct. 30, 2013, Schattka, et al.
International Search Report Issued Mar. 27, 2012 in PCT/EP11/060097 Filed Jun. 17, 2011.
Written Opinion of the International Searching Authority Issued Mar. 27, 2012 in PCT/EP11/060097 Filed Jun. 17, 2011.
Office Action issued Jul. 3, 2015 in Russian Patent Application No. 2014101228/15 (001654) (with English language translation).

(Continued)

*Primary Examiner* — Isaac Shomer
(74) *Attorney, Agent, or Firm* — Oblon, McClelland, Maier & Neustadt, L.L.P.

(57) ABSTRACT

The invention relates to a coating composition suitable for the coating of pharmaceutical or nutraceutical dosage form, comprising a core comprising one or more pharmaceutical or nutraceutical active ingredients, wherein the coating composition is comprising at least 20% by weight of an enteric core/shell polymer composition derived from an emulsion polymerization process, wherein the core of the core/shell polymer composition is formed by a water-insoluble, cross-linked polymer or copolymer and the shell of the core/shell polymer composition is formed by an anionic polymer or copolymer.

14 Claims, No Drawings

(56) References Cited

OTHER PUBLICATIONS

I.V. Pokrovskiy, "Encyclopaedic Dictionary of Medical Terms" Medicine, 2001, 6 Pages (with Cover Pages and English language translation).

* cited by examiner

COATING COMPOSITION SUITABLE FOR PHARMACEUTICAL OR NUTRACEUTICAL DOSAGE FORMS

FIELD OF THE INVENTION

The invention relates to a coating composition suitable for the coating of pharmaceutical or nutraceutical dosage form, comprising a core comprising one or more pharmaceutical or nutraceutical active ingredients, wherein the coating composition is comprising at least 20% by weight of an enteric core/shell polymer composition derived from an emulsion polymerisation process, wherein the core of the core/shell polymer composition is formed by a water-insoluble, cross-linked polymer or copolymer and the shell of the core/shell polymer composition is formed by an anionic polymer or copolymer.

TECHNICAL BACKGROUND (Meth)acrylate copolymers containing anionic groups are for instance disclosed in EP0704208B1, EP0704207A2, WO03/072087A1, WO2004/096185A1.

Controlled release pharmaceutical compositions with resistance against the influence of ethanol employing a coating comprising neutral vinyl polymers and excipients are known from WO2010/105672A1.

Controlled release pharmaceutical compositions with resistance against the influence of ethanol employing a coating comprising a polymer mixture and excipients are known from WO2010/105673A1.

PH-dependent controlled release pharmaceutical composition for narcotic drugs (opioids) with decreased susceptibility to the influence of ethanol on the release of active compound are known from WO2009/036812A1 and WO2010034342A1.

PH-dependent controlled release pharmaceutical compositions for drugs that are not opioids with decreased susceptibility to the influence of ethanol on the release of active compound are known from WO2009/036811A1 and WO2010034344A1.

WO2008/049657 describes the use of gastric resistant (meth)acrylate copolymers in retarded oral dosage forms as matrix formers for the active ingredient included in order to minimize the effect of acceleration or deceleration of the active ingredient release by the influence of ethanol under in-vitro conditions.

GENERAL DEFINITIONS

Singular forms like "a", "an", "the" or "another" as used in the description or in the claims shall be understood as to include the plural of the defined subject within the given definition or limits as well if not stated explicitly otherwise.

For instance the term "an enteric core/shell polymer composition" shall include one or more of theses compositions or copolymers e.g. mixtures thereof.

For instance the singular term "a (meth)acrylate copolymer" or "the (meth)acrylate copolymer" shall have the meaning of one or more (meth)acrylate copolymers within the given definition or limits of the monomer composition. Thus mixtures of different (meth)acrylate copolymers within the given definition or limits of the monomer composition are included in the sense of the invention. Singular terms like "a C4- to C18-alkyl ester of acrylic or methacrylic acid" or "another vinylic monomer" shall be understood in the same way to include one or more of these monomers.

Preferably the monomer ratios for copolymers disclosed herein add up to 100% by weight.

Problem and Solution

Pharmaceutical or nutraceutical compositions are designed to release the active ingredient in a manner of reproducible release curves. This shall result in desirable and reliable blood level profiles which shall provide an optimal therapeutic effect. If the blood level concentrations are too low, the active ingredient will not cause a sufficient therapeutic effect. If the blood level concentrations are too high, this may cause toxic effects. In both cases non optimal blood level concentrations of an active ingredient can be dangerous for the patient and shall therefore be avoided. A problem exists in that the ideal ratios assumed for the release of active ingredient during the design of a pharmaceutical or nutraceutical composition can be altered by the general living habits, thoughtlessness or by addictive behaviour of the patients with respect to the use of ethanol or ethanol-containing drinks. In these cases, the pharmaceutical or nutraceutical form which is actually designed for an exclusively aqueous medium is additionally exposed to an ethanol containing medium of greater or lesser strength. Since health authorities like for instance the US Food and Drug Administration (FDA) focus more and more on the ethanol problem, ethanol resistance may be an important registration requirement in the near future.

Since not all patients are aware of the risk of simultaneous taking of a controlled release pharmaceutical or nutraceutical form and ethanol-containing drinks or do not follow or are not able to follow appropriate warnings, advice or recommendations, there is a demand for controlled release pharmaceutical or nutraceutical compositions, especially for gastric resistant pharmaceutical or nutraceutical compositions, such that their mode of action is affected as little as possible by the presence of ethanol.

Conventional gastric resistant pharmaceutical or nutraceutical compositions if coated or uncoated are usually not resistant to alcohol at all. Therefore one problem of the present invention was to provide gastric resistant pharmaceutical or nutraceutical compositions which are resistant against the influence of ethanol.

Especially there is a problem for gastric resistant or enteric formulated compositions. These kinds of formulations are usually coated with a gastric resistant coating layer (enteric coating layer) onto the core which has the function that the release of the pharmaceutical or nutraceutical active ingredient in the stomach, respectively at pH 1.2 for 2 hours according to USP, shall not exceed 10, 8 or maybe 5%. This function ensures that acid-sensitive pharmaceutical or nutraceutical active ingredients are protected against inactivation and that pharmaceutical or nutraceutical active ingredients which may be irritate the stomach mucosa are not set free in too high amounts. On the other hand in many cases the release of the pharmaceutical or nutraceutical active ingredient in the intestine, respectively at pH 6.8 for one hour or less according to the USP method, is designed to exceed at least 50, 60, 80% or more. The presence of ethanol in concentrations of 20, 30 or 40% (volume/volume) in the gastric fluid usually leads to an increase to the release rates in the stomach. Due to distribution effect the effect of ingested ethanol is in the intestine not of that importance as in the stomach.

Thus an effective protection against the influence of ethanol should prevent such an undesired increase of pharmaceutical or nutraceutical active ingredient in the stomach in the first place. Furthermore it may be desired that protection against the influence of ethanol shall at least not influence the comparably fast release rates at pH 6.8 in media without ethanol.

The several problems as discussed herein are solved by a coating composition suitable for the coating of a pharmaceutical or nutraceutical dosage form, comprising a core comprising one or more pharmaceutical or nutraceutical active ingredients, wherein the coating composition is comprising at least 20% by weight of an enteric core/shell polymer composition derived from an emulsion polymerisation process, wherein the core of the core/shell polymer composition is formed by a water-insoluble, cross-linked polymer or copolymer and the shell of the core/shell polymer composition is formed by an anionic polymer or copolymer.

DETAILED DESCRIPTION OF THE INVENTION

The invention is concerned with a coating composition suitable for the coating of pharmaceutical or nutraceutical dosage form, comprising a core comprising one or more pharmaceutical or nutraceutical active ingredients, wherein the coating composition is comprising at least 20, at least 30, at least 40, at least 50, at least 60, at least 70, at least 80, at least 90 or 100% % by weight of an enteric core/shell polymer composition derived from an emulsion polymerisation process, wherein the core of the core/shell polymer composition is formed by a water-insoluble, cross-linked polymer or copolymer and the shell of the core/shell polymer composition is formed by an anionic polymer or copolymer.

Food Grade or Pharmaceutical Grade Requirements

Suitable for the coating of a pharmaceutical or nutraceutical dosage form shall mean that the coating or binding composition shall fulfil all general and specific food grade or pharmaceutical grade requirements, including regulatory and legal requirements, for pharmaceutical or nutraceutical dosage forms. Of course all further excipients used in the pharmaceutical or nutraceutical dosage forms described herein shall also fulfil all general and specific food grade or pharmaceutical grade requirements, including regulatory and legal requirements, for pharmaceutical or nutraceutical dosage forms as well.

Coating Composition

The invention is concerned with a coating composition suitable for the coating of a pharmaceutical or nutraceutical dosage form, wherein the coating or binding composition is comprising at least 20, at least 30, at least 40, at least 50, at least 60, at least 70, at least 80, at least 90 or 100% by weight of an enteric core/shell polymer composition derived from an emulsion polymerisation process, wherein the core is formed by a water-insoluble, cross-linked polymer or copolymer and the shell is formed an anionic polymer or copolymer.

Aqueous Dispersion

The enteric core/shell polymer composition may be present in the coating composition in form of the solid phase of an aqueous dispersion with a solid content from 1 to 60% by weight. This means that the aqueous polymer dispersion, that is used to prepare the coating formulation, may contain 1 to 70% by weight of the coating composition as solid phase and 30 to 99% by weight as aqueous phase.

Powder or a Granulate

The enteric core/shell polymer composition may be present in the coating composition in the form of a dry powder or a granulate. In comparison to dispersion powders or a granulates have the advantage of less weight and less volume and can be stored in the dry stage for a long time without the risk of coagulation or of microbial contamination.

The solid from such an aqueous dispersion may be isolated by a spray drying process, freeze drying process or a coagulation process to give dry powder or a granulates. The powders or granulates may be converted into an aqueous dispersion again by redispersion in water.

Emulsion Polymerisation Process

In a typical emulsion polymerisation process first a core in the form of core particles is formed by polymerisation of the monomers for polymer or the copolymer of the core. Subsequently the monomers for polymer or the copolymer of the shell are polymerized in the same reaction mixture to give a shell around on the surface of the core particles.

In the emulsion polymerization process, the operation may advantageously be carried out by the monomer emulsion feed process or the monomer feed process, respectively. For this, water is heated to the reaction temperature in the polymerization reactor. Surfactants and/or initiators may be added at this stage. Then—depending on the mode of operation—the monomer, a monomer mixture or an emulsion of either are fed to the reactor. This dosed liquid may contain initiators and/or surfactants or the initiator and/or the surfactant may be dosed parallel.

Alternatively, all monomers for the core can be charged into the reactor, before adding the initiator. This method is often referred to as batch process.

A chain transfer agent may be added to improve the process stability and reproducibility of the molecular weight ($M_w$). A usual chain transfer agent amount may be 0.05 to 1% by weight. A typical chain transfer agent may be for example thioglycolic acid 2-ethyl hexyl ester (TGEH) or n-dodecyl mercaptane (nDDM). However the chain transfer agent may be omitted in many cases, without affecting the properties according to the invention.

It is also possible to do a combination of both processes, by polymerizing a part of the monomers in the manner of a batch process, and feeding the other part afterwards. As known to the expert in the field, the type of process and mode of operation can be chosen, to achieve the desired particle size, sufficient dispersion stability, a stable production process and so on.

The average particle size of the polymer particles produced in the emulsion polymerization may range from 10 to 1000, 20 to 500 or 50 to 250 nm. The average particle size of the polymer particles may be determined by methods well known to a skilled person for instance by the method of laser diffraction. The particle size may be determined by laser diffraction, using a Mastersizer® 2000 (Malvern). The values can be indicated as particle radius rMS [nm], which is half of the median of the volume based particle size distribution d(v,50).

Emulsifiers which may be used are especially anionic and non-ionic surfactants. The amount of emulsifier used is generally not more than 5% by weight, based on the polymer. Typical surfactants are for example alkyl sulfates (e.g. sodium dodecyl sulfate), alkyl ether sulfates, dioctyl sodium sulfosuccinate, polysorbates (e.g. polyoxyethylene (20) sorbitan monooleate), nonylphenol ethoxylates (nonoxynol-9) and others.

Beside those initiators conventionally used in emulsion polymerization (e.g. per-compounds, such as ammonium peroxodisulfate (APS), redox systems, such as sodium disulphite-APS-iron can be applied. Also water soluble azoinitiators may be applied and/or a mixture of initiators can be used. The amount of initiator is usually between 0.005 to 0.5% by weight, based on the monomer weight.

The polymerization temperature depends on the initiators within certain limits. For example, if APS is used it is advantageous to operate in the range from 60 to 90° C.; if redox systems are used it is also possible to polymerize at lower temperatures, for example at 30° C.

Enteric Core/Shell Polymer Composition

The core/shell polymer composition of the present invention has enteric properties. This mean the core/shell polymer composition is gastric resistant with no dissolution but swelling at acidic pH values, for instance at pH 1 to 4, but dissolves more or less rapidly at higher pH values, for instance from pH 5.0 on or higher. By being enteric the core/shell polymer composition confers gastric resistance and rapid active ingredient release in the intestine to the pharmaceutical or nutraceutical dosage form to or at which it is applied as a coating or as a binding agent. As a further advantage the core/shell polymer composition also confers gastric resistance in the presence of ethanol in the stomach.

A core/shell polymer composition is derived from an emulsion polymerisation process in at least two steps. In the first process step core polymer particles are formed by monomer polymerisation in the emulsion. In the second step the shell is polymerized onto these core particles by subsequent monomer polymerisation in the same emulsion.

The invention relates to a core/shell polymer composition suitable as a coating or binding agent in a pharmaceutical or nutraceutical dosage form, where the core/shell polymer composition is derived from an emulsion polymerisation process, wherein the core is formed by a water-insoluble, cross-linked polymer or copolymer and the shell is formed an anionic polymer or copolymer.

The invention discloses explicitly each possible combination of any water-insoluble, cross-linked polymer or copolymer described in here as a core polymer or copolymer with any anionic polymer or copolymer described in here as a shell polymer or copolymer.

The polymer or copolymer of the core is cross-linked. Cross-linked means that the polymer or copolymer is polymerized at least partially from monomers containing two or more reactive groups or one or more reactive side groups which are capable to cross-link the linear polymer chains. Reactive groups or side groups which are capable to cross-link the linear polymer chains may be a vinylic group or an allylic group. For example monomers with more than one vinylic group or with one vinylic and one or more allylic groups may be used. For instance ethyleneglycol-di-methacrylate (EGDMA) may be used as a cross-linking monomer. For cross-linked polymers, it is usually not possible to find a solvent to dissolve them.

The polymer or copolymer of the shell is usually not cross-linked and thus may be linear.

Core/Shell Ratios

The weight of the core may be 10 to 95% of the weight of the total core/shell polymer composition.

The core/shell polymer composition may comprise, comprise essentially or consist of 10 to 95, or 20 to 90, preferably 30 to 80% by weight of the polymers or copolymers of the core. The core/shell polymer composition may comprise, comprise essentially or consist of 5 to 90, or 10 to 80, preferably 20 to 70% by weight of the polymers or copolymers of the shell. Core and shell may add up to 100%. Usually there is one core and one shell in the core/shell polymer composition. However it is also possible that more than one shell, i.e. two or more different shell polymers or copolymers may be applied to one core polymers or copolymers.

It has been surprisingly found that standard, non-core/shell enteric polymer coatings can be substituted by coatings of the same thickness, based on the core/shell polymer compositions as disclosed without impairing the enteric properties. Furthermore the resistance against ethanol is improved. At the same time the total amount of anionic groups in the coating is reduced. This is of further advantage because the maximum daily intake for which the amount of anionic groups is usually limiting can be increased.

Different Micro Structural and Physical Behaviour

Due to their mode of preparation the core/shell polymer composition according to the present invention show a different micro structural and also a different physical behaviour compared to simple mixtures of the same two polymers or copolymers at the same weight ratios. As each polymer particle of the core/shell dispersion contains both core and shell polymer, the two polymers are evenly distributed from the very start. In contrast, for a physical mixture of two polymer dispersions, particles of one and the other polymer are distributed randomly; adjacent particles of the same polymer are forming larger domains.

The difference in the microstructure may in certain cases be visualized under a light microscope where the core/shell polymer compositions may show a more homogeneous structure without visible phase separation. The difference in the physical behaviour may show in a more or less unique intermediate glass transition temperature compared to two glass transition temperature peaks in the simple mixtures. Thus core/shell polymer compositions of the present invention result in more homogenous mixtures of the two polymers than it can be achieved with pure physically mixtures or simple mixtures. This apparently results in more homogenous coatings with an assumed finer microstructure. Fewer incompatibilities between the two polymers occur. Coated pharmaceutical or nutraceutical drug forms become more reliable in their active ingredient release behaviour and more stable under storage conditions. Positive effects on the tensile strength and differences in the film forming temperatures may be also observed.

Core Polymer or Copolymer

Water-Insoluble, Cross-Linked Polymers or Copolymers

A suitable water-insoluble, cross-linked copolymer for the formation of the core of the enteric core/shell polymer composition may be polymerized from cross-linking monomers alone or preferably from cross-linking and non-cross-linking monomers. Suitable amounts of cross-linking monomers may be in the range of 0.1 to 100, 0.2 to 10, 0.2 to 5, preferably 0.3 to 3% by weight calculated on the total amount of monomers used for the core polymer or copolymer.

A suitable water-insoluble, cross-linked copolymer for the formation of the core of the enteric core/shell polymer composition may be polymerized from 98-99.9, preferably 99.6% by weight n-butyl acrylate (n-BA) and 0.1-2, preferably 0.4% by weight ethyleneglycol-di-methacrylate (EGDMA)

Another suitable water-insoluble, cross-linked copolymer for the formation of the core of the enteric core/shell polymer composition may be polymerized from 99.6% methyl methacrylate (MMA) and 1.5% EGDMA.

Shell Polymer or Copolymer

Anionic Polymer or Copolymers

The anionic polymer or copolymer which may be preferably used as the shell of the enteric core/shell composition may be selected from the group of (meth)acrylate polymers or copolymers or polyvinyl polymers or copolymers.

Anionic Polyvinyl Polymers

Suitable polyvinyl polymers or copolymers may comprise structural units that are derived from unsaturated carboxylic acids other than acrylic acid or methacrylic acid as exemplified by polyvinylacetatephthalate or a copolymer of vinylacetate and crotonic acid 9:1.

Anionic (Meth)Acrylate Copolymers

Anionic (meth)acrylate copolymers may comprise 25 to 95, preferably 40 to 95, in particular 60 to 40, % by weight free-radical polymerized $C_1$- to $C_{18}$-alkyl esters, preferably $C_1$- to $C_8$ or $C_1$- to $C_4$ alkyl esters of alkyl esters of acrylic or of methacrylic acid and 75 to 5, preferably 60 to 5, in particular 40 to 60, % by weight (meth)acrylate monomers having an anionic group.

The proportions mentioned normally add up to 100% by weight. However it is also possible in addition, without this leading to an impairment or alteration of the essential properties, for small amounts in the region of 0 to 20 or 0 to 10, for example 1 to 5% by weight of further monomers capable of vinylic copolymerization, such as, for example, hydroxyethyl methacrylate or hydroxyethyl acrylate, to be present. It is preferred that no further monomers capable of vinylic copolymerization are present.

$C_1$- to $C_4$-alkyl esters of acrylic or methacrylic acid are in particular methyl methacrylate, ethyl methacrylate, butyl methacrylate, methyl acrylate, ethyl acrylate and butyl acrylate. A (meth)acrylate monomer having an anionic group is, for example, acrylic acid, with preference for methacrylic acid.

Examples for Suitable Anionic (Meth)Acrylate Copolymers

A suitable anionic (meth)acrylate copolymer may be comprising, essentially comprising, containing or consisting of polymerized units of
  10 to 40% by weight of acrylic or methacrylic acid
  10 to 80% by weight of a $C_4$- to $C_{18}$-alkyl ester of acrylic or methacrylic acid and optionally
  0 to 60% by weight of another vinylic monomer.

$C_4$- to $C_{18}$-alkyl ester of acrylic or methacrylic acid are preferably chosen from n-butyl methacrylate, 2-ethylhexyl acrylate, 2-ethylhexyl methacrylate, isodecyl methacrylate and lauryl methacrylate.

Another vinylic monomer is a monomer which is not acrylic or methacrylic acid or a $C_4$- to $C_{18}$-alkyl ester of acrylic or methacrylic acid. Another vinylic monomer may be preferably $C_1$- to $C_3$-alkyl ester of acrylic or methacrylic acid, which are methyl acrylate, ethyl acrylate, propyl acrylate, methyl methacrylate, ethyl methacrylate or propyl methacrylate. Another vinylic monomer may be hydroxyethyl methacrylate, hydroxypropyl methacrylate, poly(ethylenglycol)methylether acrylat, poly(ethylenglycol)methylether methacrylat, poly(propylenglycol)methylether acrylat, poly(propylenglycol)methylether methacrylat or styrene.

Preferably the anionic (meth)acrylate copolymer is comprising, essentially comprising or containing polymerized units of
  10 to 40% by weight of acrylic or methacrylic acid
  10 to 50% by weight of ethyl acrylate
  10 to 80% by weight of a $C_4$- to $C_{18}$-alkyl ester of acrylic or methacrylic acid and optionally
  0 to 20 by weight of methyl methacrylate.

Preferably the anionic (meth)acrylate copolymer is comprising, essentially comprising or containing polymerized units of
  20 to 40% by weight of methacrylic acid,
  20 to 40% by weight of n-butyl methacrylate and
  30 to 50% by weight of ethyl acrylate Preferably the anionic (meth)acrylate copolymer is comprising, essentially comprising or containing polymerized units of
  20 to 40% by weight of methacrylic acid,
  30 to 50% by weight of 2-ethylhexyl acrylate,
  15 to 40% by weight of ethyl acrylate and optionally
  0 to 20% by weight of methyl methacrylate.

Preferably the anionic (meth)acrylate copolymer is comprising, essentially comprising or containing polymerized units of
  10 to 40% by weight of methacrylic acid,
  20 to 70% by weight of 2-ethylhexyl methacrylate and
  10 to 50% by weight of ethyl acrylate.

Preferably the anionic (meth)acrylate copolymer is comprising, essentially comprising or containing polymerized units of
  20 to 40% by weight of methacrylic acid,
  20 to 50% by weight of 2-ethylhexyl methacrylate and
  20 to 50% by weight of ethyl acrylate.

Preferably the anionic (meth)acrylate copolymer is comprising, essentially comprising or containing polymerized units of
  10 to 35% by weight of methacrylic acid,
  40 to 70% by weight of 2-ethylhexyl methacrylate and
  10 to 30% by weight of ethyl acrylate.

Preferably the anionic (meth)acrylate copolymer is comprising, essentially comprising or containing polymerized units of
  20 to 40% by weight of methacrylic acid,
  20 to 40% by weight of isodecyl methacrylate and
  40 to 50% by weight of ethyl acrylate.

Preferably the anionic (meth)acrylate copolymer is comprising, essentially comprising or containing polymerized units of
  20 to 40% by weight of methacrylic acid,
  20 to 40% by weight of lauryl methacrylate and
  30 to 50% by weight of ethyl acrylate.

Further Characteristics of the Anionic (Meth)Acrylate Copolymer,

Further characteristics of the anionic (meth)acrylate copolymer, especially of the anionic (meth)acrylate copolymers described above may be summarized as follows.

Preferably the (meth)acrylate copolymer may be characterized by a mean glass transition temperature from 25 to 120 or 40 to 80° C. (determined by DSC according to DIN EN ISO 11357).

Preferably the (meth)acrylate copolymer may be characterized by a minimum film forming temperature of 50° C. or less (determined according to DIN ISO 2115).

Preferably the (meth)acrylate copolymer may be characterized by a mean molecular weight $M_w$ is 80.000 or more (determined by gel permeation chromatography (GPC)).

Further Suitable Anionic (Meth)Acrylate Copolymer

Suitable anionic (meth)acrylate copolymers are those composed of 40 to 60% by weight methacrylic acid and 60 to 40% by weight methyl methacrylate or 60 to 40% by weight ethyl acrylate (EUDRAGIT® L or EUDRAGIT® L100-55 types).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable is a copolymer composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate 0 to 10% by weight further monomers capable of vinylic copolymerization,
where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of
20 to 33, preferably 25 to 32, particularly preferably 28 to 31% by weight methacrylic acid or acrylic acid, with preference for methacrylic acid,
5 to 30, preferably 10 to 28, particularly preferably 15 to 25% by weight methyl acrylate,
20 to 40, preferably 25 to 35, particularly preferably 18 to 22% by weight ethyl acrylate, and
more than 10 to 30, preferably 15 to 25, particularly preferably 18 to 22% by weight butyl methacrylate,
where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

Preparation of Anionic (Meth)Acrylate Copolymers

The anionic (meth)acrylate copolymers may be prepared in a manner known per se by free-radical polymerization of the monomers (see, for example, EP 0 704 207 A2 and EP 0 704 208 A2) by radical polymerisation of the monomers in the presence of polymerisation initiators and optionally molecular weight regulators. The copolymers according to the invention are prepared by free-radical emulsion polymerization in aqueous phase in the presence of, preferably, anionic emulsifiers. The process of emulsion polymerization is well known in the art for instance as described in DE-C 2 135 073.

The average molecular weight Mw (weight average, determined for example by measuring the solution viscosity) of the anionic (meth)acrylate copolymers may be for example in the range from 80 000 to 1 000 000 (g/mol).

Process for Preparing an Anionic (Meth)Acrylate Copolymer

An anionic (meth)acrylate copolymer may be produced by radical polymerisation of the monomers in the presence of polymerisation initiators. Molecular weight regulators may be added. The preferred polymerisation method is emulsion polymerisation.

Suitable Core/Shell Combinations

Combination 1: Core Polymer C1 with Shell Polymer S1:

Core Polymer C1:
Copolymer out of
95.0-99.9, preferably 99.6% by weight n-butyl acrylate (n-BA) and
0.1-5.0, preferably 0.4% by weight ethyleneglycol-di-methacrylate (EGDMA)

Shell Polymer S1:
Copolymer out of
30-50, preferably 35-45, especially 40% by weight ethyl acrylate (EA),
20-40, preferably 25-35, especially 30% by weight 2-ethylhexyl methacrylate (EHMA) and
20-40, preferably 25-35, especially 30% by weight methacrylic acid (MAS)

Release of the Pharmaceutical or Nutraceutical Active Ingredient for the Coating Composition The release of the pharmaceutical or nutraceutical active ingredient, according to USP, is not more than 10, not more than 8 or not more than 5% under in-vitro conditions at pH 1.2 after 2 hours in 0.1 molar HCl with and without the addition of 20, 30 or 40% (v/v) ethanol.

The release of the pharmaceutical or nutraceutical active ingredient, according to USP, is at least 50, at least 60, at least 80% under in-vitro conditions at pH 6.8 after 45 or after 60 minutes in buffered medium (phosphate buffered saline, pH 6.8, European Pharmacopoeia 4003200).

Alternatively the release of the pharmaceutical or nutraceutical active ingredient may be at least 50, at least 60, at least 80% under in-vitro conditions at pH 7.2 after 45 or after 60 minutes in buffered medium according to USP for instance when copolymers of the EUDRAGIT® FS type are used as shell polymers. EUDRAGIT® FS type copolymers show a start of the specific active ingredient release in intestinal juice or simulated intestinal fluid around pH 7.0.

Thus the release of the pharmaceutical or nutraceutical active ingredient may be at least 50, at least 60, at least 80% under in-vitro conditions at pH 6.8 or at pH 7.2 after 45 or after 60 minutes in buffered medium according to USP.

The USP (USP=United States Pharmacopoeia) which may be preferably used is USP32/NF27 (NF=National Formulary), apparatus II, paddle method, 50 rpm for tablets or paddle or basket method (apparatus I) 50 to 100 rpm, depending on the monograph, for pellets.

Core Comprising the Pharmaceutical or Nutraceutical Active Ingredient

The core comprises one or more pharmaceutical or nutraceutical active ingredients as the core or as a part of the core. The one or more pharmaceutical or nutraceutical active ingredients may be more or less homogeneously distributed in a matrix structure within the core structure or may form the core as a crystallized structure. The one or more pharmaceutical or nutraceutical active ingredients may alternatively be present as a part of the core in the form of a layer onto a carrier pellet. Thus the core is an unfinished, coated or uncoated, but still to be coated pharmaceutical or nutraceutical dosage form.

The core, respectively the pharmaceutical or nutraceutical dosage form to be coated by the coating composition may comprise or may contain a neutral carrier pellet, for instance a sugar sphere or non-pareilles, on top of which the active ingredient is bound in a binder, such as lactose or polyvinyl pyrrolidon.

The core may alternatively comprise a pellet in the form of a polymeric matrix in which the active ingredient is bound. The core may comprise an uncoated pellet consisting of a crystallized active ingredient. The core may also comprise its own coating for instance a sustained release coating. Such an already coated core may then be coated by the coating composition described herein.

The core may be uncoated or may comprise a coating, which is different from the coating derived from coating composition described herein. The core may be a coated pellet, for instance with a sustained release coating, an uncoated or coated tablet, an uncoated or coated mini tablet or an uncoated or coated capsule. The core may also comprise a so called "sub coat" as an outer layer.

The core comprises at least more than 80, more than 90, more than 95, more than 98, preferably 100% of the total amount of one or more pharmaceutical or nutraceutical active ingredients present in the gastric resistant pharmaceutical or nutraceutical dosage form.

In some cases it may be useful that the coating composition may comprise, additionally to the active ingredient present in the core, a partial amount, preferably less than 20, less than 10, less than 5 less than 2% by weight of the total amount of one or more pharmaceutical or nutraceutical active ingredients, for instance in order to provide an initial dose of the active ingredient. In this case the coating composition has the function as a binding agent or as a binder for the additional active ingredient. Preferably the coating composition comprises any active ingredient.

Coating

Coating suspensions may be applied by spray or powder coating processes following known processes. As a rule the coated compositions may be cured at elevated temperatures for example 24 hours at 40° C. or 60° C. after the spray coating in order to provide reproducible and stable functionality.

The polymer dry weight gain of the coating layer may be at least 2.5, at least 3.5, at least 4, preferably 4 to 30, preferably 4 to 20, more preferably 5 to 18, or most preferably 10 to 18 mg/cm$^2$ surface area. This may correlate to 2-60% polymer dry weight gain related to the weight of the core. In the case of coated tablets the polymer dry weight gain related to the weight of the core (tablet core: around 1-25 or 1-10 mm in diameter or length) may be 2-30%. In the case of coated pellets the polymer dry weight gain related to the weight of the core (pellet core: 0.1 to 1.5 mm in diameter) may be 10-60%.

Pellets are typically coated with at least 4 weight % of polymer, based on the weight of the uncoated pellets (i.e. 4% polymer weight gain). A better protection of the active ingredient is achieved with a thicker coating of 6%, 8% or 10% polymer weight gain.

Usually not more than 40% polymer weight gain of coating are applied to pellets, as then the time for the dissolution of the coating layer starts getting too long. In many cases less than 30%, less than 25%, or less than 20% polymer weight gain are sufficient.

On tablets and capsules, a coating with typically at least 2 mg polymer per cm$^2$ of surface is applied. In most cases at least 3 mg, 4 mg or 6 mg of polymer per cm$^2$ of surface are applied. Coating amounts of more than 40 mg of polymer per cm$^2$ of surface are hardly ever used; typically less than 30 mg, less than 25 mg or less than 20 mg of polymer per cm$^2$ of surface are applied. In general more coating thickness is required for capsules and oblong shaped tablets, while more spherical dosage forms require less coating.

Top Coat and Sub Coats

The gastric resistant pharmaceutical or nutraceutical dosage according to the invention may further comprise a so called "sub coat" or a so called "top coat" or both. The expressions sub coat and top coat are well known to the person skilled in the art.

A sub coat may be added as an outer layer of the pharmaceutical or nutraceutical active ingredient core below the gastric resistant (enteric) coating layer. The sub coat may have the function to separate substances of the core, for instance the active ingredient, from substances of the coating layer which may be incompatible with each other. The sub coat has essentially no influence on the active ingredient release characteristics. The subcoat is preferably essentially water-soluble, for instance it may consist of substances like hydroxypropylmethyl-cellulose (HPMC) as a film former. The average thickness of the subcoat layer is very thin, for example not more than 15 μm, preferably not more than 10 μm.

A top coat may be present on top of the enteric coating layer and may be also preferably essentially water soluble. The top coat may have the function of colouring the pharmaceutical or nutraceutical form or protecting from environmental influences for instance from moisture during storage. The top coat may consist out of a binder, for instance a water soluble polymer like a polysaccharide or HPMC, or a sugar compound like saccharose. The top coat may further contain pharmaceutical or nutraceutical excipients like pigments or glidants in high amounts. The topcoat has essentially no influence on the release characteristics.

Pharmaceutical or Nutraceutical Active Ingredients
Nutraceutical Active Ingredients The invention is preferably useful for nutraceutical dosage forms.

Nutraceuticals can be defined as extracts of foods claimed to have medical effects on human health. The nutraceutical is usual contained in a medical format such as capsule, tablet or powder in a prescribed dose. Examples for nutraceutical active ingredients are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flvonoids, antioxidants, alpha-linoleic acid from flax seed, beta-carotene from marigold petals or antocyanins from berries. Sometimes the expression neutraceuticals is used as synonym for nutraceuticals.

The gastric resistant pharmaceutical or nutraceutical composition is comprising a core, comprising a pharmaceutical or nutraceutical active ingredient. The pharmaceutical or nutraceutical active ingredient may be a pharmaceutical or nutraceutical active ingredient which may be inactivated under the influence of gastric fluids at pH 1.2 or a pharmaceutical or nutraceutical active ingredient which may irritate the stomach mucosa when set free in the stomach.

Pharmaceutical Active Ingredients

The invention is also preferably useful for enteric coated pharmaceutical dosage forms.

Preferred drug classes are those (including but not limited to) coming from parenteral to oral switch considerations and/or high potency drugs (e.g. cytostatics, hormons, hormon receptor agonists, hormon receptor antagonists) and/or drugs with high side effects and toxicity issues (including prodrug metabolization; e.g. peptides, peptidomimetics, nucleotides, nucloesides, nucloeside analogues, taxoids)

Especially preferred are the following drugs
Remicade® (Infliximab, Johnson & Johnson, Schering-Plough, Mitsubishi Tanabe Pharma—Crohn's disease, Rheumatoid arthritis),
Enbrel® (Etanercept, Wyeth—Rheumatoid arthritis),
Zyprexa® (Olanzapine, Eli Lilly and Company—Psychosis),
Seroquel® (Quetiapine, AstraZeneca—Schizophrenia),
Herceptin® (Trastuzumab, Roche, Genentech, Chugai Pharmaceutical—Breast cancer),
Lexapro®, Cipralex® (Escitalopram, Forest Laboratories, H. Lundbeck—Depression, Anxiety disorders),
Gleevec®, Glivec (Imatinib, Novartis—Leukemia),
Avastin® (Bevacizumab, Roche, Genentech—Colorectal cancer),
Taxotere® (Docetaxel, Sanofi-Aventis—Cancer),
Eloxatin®, Eloxatine® (Oxaliplatin, Sanofi-Aventis—Colorectal cancer),
Wellbutrin® (Bupropion, GlaxoSmithKline, Biovail—Depression, Seasonal affective disorder (SAD)),
Abilify® (Aripiprazole, Otsuka Pharmaceutical, Bristol-Myers Squibb—Psychosis, Depression),
Avonex® (Interferonbeta-1a, Biogen Idec—Multiple sclerosis),
Viagra® (Sildenafil, Pfizer—Erectile dysfunction),
Lupron®, Leuplin (Leuprolide, Takeda Pharmaceutical, TAP Pharmaceuticals—Prostate cancer),
Zofran® (Ondansetron, GlaxoSmithKline—Nausea and vomiting),
Arimidex® (Anastrozole, AstraZeneca—Breast cancer),
Prograf® (Tacrolimus, Astellas Pharma—Transplant rejection),
CellCept® (Mycophenolatemofetil, Roche, Chugai Pharmaceutical—Transplant rejection),
Gemzar® (Gemcitabine, Eli Lilly and Company—Cancer),
Cymbalta® (Duloxetine, Eli Lilly and Company—Depression, Anxiety disorders),
Duragesic® (Fentanyl, Johnson & Johnson—Pain),
Casodex® (Bicalutamide, AstraZeneca—Prostate cancer),
Truvada® (Tenofovir+Emtricitabine, Gilead Sciences—HIV infection),
Flomax® (Tamsulosin, Boehringer Ingelheim—Benign prostatic hypertrophy),
Lyrica® (Pregabalin, Pfizer—Neuropathic pain),
Paxil®, Seroxat® (Paroxetine, GlaxoSmithKline—Depression, Anxiety disorders),
Kaletra® (Lopinavir, Abbott Laboratories—HIV infection),
Erbitux® (Cetuximab, Bristol-Myers Squibb, Merck KGaA—Colorectal cancer),
Zoladex® (Goserelin, AstraZeneca—Prostate cancer),
Combivir® (Lamivudine+Zidovudine, GlaxoSmithKline—HIV infection),
Clalis® (Tadalafil, Eli Lilly and Company, Lilly Icos—Erectile dysfunction),
Reyataz® (Atazanavir, Bristol-Myers Squibb—HIV infection),
Concerta® (Methylphenidate, Johnson & Johnson—Attention-deficit hyperactivity disorder),
Camptosar® (Irinotecan, Pfizer—Colorectal cancer),
Adderall® (Amphetamine, Shire Pharmaceuticals—Attention-deficit hyperactivity disorder),
Ultane®, Sevorane® (Sevoflurane, Abbott Laboratories—Anesthesia),
Xeloda® (Capecitabine, Roche, Chugai Pharmaceutical—Cancer),
Femara® (Letrozole, Novartis, Chugai Pharmaceutical—Breast cancer),
Viread® (Tenofovir, Gilead Sciences—HIV infection),
Tarceva® (Erlotinib™, Roche, Genentech—Non-small cell lung cancer),
Alimta® (Pemetrexed™, Eli Lilly and Company—Non-small cell lung cancer),
Actiq® (Fentanyl, Cephalon—Cancer pain),
Lidoderm® (Lidocaine, Endo Pharmaceuticals—Pain),
Taxol® (Paclitaxel, Bristol-Myers Squibb—Cancer),
Trizivir® (Abacavir+Lamivudine+Zidovudine, GlaxoSmithKline—HIV infection),
Epzicom®, Kixeva® (Abacavir+Lamivudine, GlaxoSmithKline—HIV infection),
Venlafaxine® (Effexor, Wyeth—Antidepressant).

. . . as well as drugs of the respective compound class thereof and/or the respective mode of action implied by said examples (as the latter is a descriptor of not only the physico-chemistry of the active pharmaceutical ingredient (API) but also its physiological behaviour and pharmaceutical character).

Therapeutical and chemical classes of drugs used in enteric coated pharmaceutical dosage forms are for instance analgetics, antibiotics or anti-infectives, antibodies, antiepileptics, antigens from plants, antirheumatics, betablocker, benzimidazole derivatives, beta-blocker, cardiovascular drugs, chemotherapeuitcs, CNS drugs, digitalis glycosides, gastrointestinal drugs, e.g. proton pum inhibitors, enzymes, hormons, liquid or solid natural extracts, oligonucleotides, peptidhormon proteins, therapeutical bacteria, peptides, proteins, proton pump inhibitors, (metal)salt f.e. aspartates, chlorides, orthates, urology drugs, vaccines Examples of drugs, which are acid-lablile, irritating or need controlled release, may be: Acamprosat, aescin, amylase, acetylsalicylic acid, adrenalin, 5-amino salicylic acid, aureomycin, bacitracin, balsalazine, beta carotene, bicalutamid bisacodyl, bromelain, bromelain, budesonide, calcitonin, carbamacipine, carboplatin, cephalosporins, cetrorelix, clarithromycin, chloromycetin, cimetidine, cisapride, cladribine, clorazepate, cromalyn, 1-deaminocysteine-8-D- arginine-vasopressin, deramciclane, detirelix, dexlansoprazole, diclofenac, didanosine, digitoxin and other digitalis glycosides, dihydrostreptomycin, dimethicone, divalproex, drospirenone, duloxetine, enzymes, erythromycin, esomeprazole, estrogens, etoposide, famotidine, fluorides, garlic oil, glucagon, granulocyte colony stimulating factor (G-CSF), heparin, hydrocortisone, human growth hormon (hGH), ibuprofen, ilaprazole, insulin, Interferon, Interleukin, Intron A, ketoprofen, lansoprazole, leuprolidacetat lipase, lipoic acid, lithium, kinin, memantine, mesalazine, methenamine, milameline, minerals, minoprazole, naproxen, natamycin, nitrofurantion, novobiocin, omeprazole, orothates, pancreatin, pantoprazole, parathyroidhormone, paroxetine, penicillin, perprazol, pindolol, polymyxin, potassium, pravastatin, prednisone, preglumetacin progabide, pro-somatostatin, protease, quinapril, rabeprazole, ranitidine, ranolazine, reboxetine, rutosid, somatostatin streptomycin, subtilin, sulfasalazine, sulphanilamide, tamsulosin, tenatoprazole, thrypsine, valproic acid, vasopressin, vitamins, zinc, including their salts, derivatives, polymorphs, isomorphs, or any kinds of mixtures or combinations thereof.

Pharmaceutical or Nutraceutical Excipients

The coating composition may comprise may comprise, essentially comprise or contain up to 80, up to 70, up to 60, up to 50, up to 40, up to 30, up to 20% by weight or any pharmaceutical or nutraceutical excipients. Thus the amounts of the enteric core/shell polymer and the pharmaceutical or nutraceutical excipients may add up to 100% in the coating composition.

In some cases it may be useful that the coating composition may also comprise, additionally to the active ingredient in the core, a partial amount, preferably less than 10% less than 5% less than 2% by weight of the total amount of one or more pharmaceutical or nutraceutical active ingredients, for instance in order to provide a fast released initial dose. In this case the coating composition has the function as a binding agent or as a binder for the additional portion of active ingredient. Thus in this case the amounts the enteric core/shell polymer, the pharmaceutical or nutraceutical excipients and the one or more pharmaceutical or nutraceutical active ingredients may add up to 100% in the coating composition.

The coating composition may comprise up to 80, up to 70, up to 60, up to 50, up to 40, up to 30, up to 20% by weight or any of pharmaceutical or nutraceutical excipients selected from the group of antioxidants, brighteners, binding agents, different from the core/shell polymers described herein, flavouring agents, flow aids, fragrances, glidants, penetration-promoting agents, pigments, plasticizers, polymers, different from the core/shell polymers described herein, pore-forming agents or stabilizers.

Gastric Resistant Pharmaceutical or Nutraceutical Dosage Form

The invention relates to a gastric resistant pharmaceutical or nutraceutical dosage form, comprising a core, comprising one or more pharmaceutical or nutraceutical active ingredients and a gastric resistant coating layer onto the core, wherein the gastric resistant coating layer is applied in a coating process employing the coating composition as described herein.

The gastric resistant pharmaceutical or nutraceutical dosage form according to the invention is characterized by the release of the pharmaceutical or nutraceutical active ingredient which is not more than 10, not more than 8 or not more than 5% under in-vitro conditions at pH 1.2 after 2 hours in medium according to USP with and without the addition of 20% (v/v) ethanol.

The gastric resistant pharmaceutical or nutraceutical composition according to the invention may be further characterized by the release of the pharmaceutical or nutraceutical active ingredient which is at least 50, at least 60, at least 80% under in-vitro conditions at pH 6.8 after 45 minutes in a buffered medium according to USP.

Reference is made to USP32/NF27 (NF=National Formulary), apparatus II, paddle method, 50 rpm for tablets or paddle or basket method 50 to 100 rpm, depending on the monograph, for pellets.

Use as a Coating Composition

The invention relates to the use of a use of a coating composition as described herein for the coating of the core of a pharmaceutical or nutraceutical dosage form to be coated, where the core is comprising a pharmaceutical or nutraceutical active ingredient, wherein the resulting coated core respectively the coated pharmaceutical or nutraceutical dosage form shows a release of the pharmaceutical or nutraceutical active ingredient of not more than 10% under in-vitro conditions at pH 1.2 after 2 hours in medium according to USP with and without the addition of 20% (v/v) ethanol Use as a Binding Composition The coating composition as described in here may as well be used as a binding agent for the binding of a pharmaceutical or nutraceutical active ingredient in a coating or in the core of a pharmaceutical or nutraceutical dosage form. When the coating composition is not used in a coating but used as a binding agent in the core of a pharmaceutical or nutraceutical dosage form, as a binder or as a matrix former, it may be rather called a binding composition.

Release of the Pharmaceutical or Nutraceutical Active Ingredient for the Binding Composition The release of the pharmaceutical or nutraceutical active ingredient is not more than 10, not more than 8 or not more than 5% under in-vitro conditions at pH 1.2 after 2 hours in medium according to USP with and without the addition of 20, 30 or 40% (v/v) ethanol.

The release of the pharmaceutical or nutraceutical active ingredient is at least 50, at least 60, at least 80% under in-vitro conditions at pH 6.8 after 45 or after 60 minutes in buffered medium according to USP.

The USP (USP=United States Pharmacopoeia) which may be preferably used is USP32/NF27 (NF=National Formulary), apparatus II, paddle method, 50 rpm for tablets or paddle or basket method 50 to 100 rpm, depending on the monograph, for pellets.

Core/Shell Polymer Composition

The invention also relates to a core/shell polymer composition as described herein for use as a coating or binding agent in a pharmaceutical or nutraceutical dosage form.

The core/shell polymer composition is derived from an emulsion polymerisation process, wherein the core is formed by a water-insoluble, cross-linked polymer or copolymer and the shell is formed an anionic polymer or copolymer.

The invention also relates to a core/shell polymer composition, suitable as coating or binding agent in a pharmaceutical or nutraceutical dosage form, comprising a core and an outer coating, where the core is comprising one or more pharmaceutical or nutraceutical active ingredients and where the coating is comprising the core/shell polymer composition, which is derived from an emulsion polymerisation process, wherein the core of the core/shell polymer composition is formed by a water-insoluble, cross-linked polymer or copolymer and the shell is formed an anionic polymer or copolymer. Thus the core/shell polymer composition is a part of the pharmaceutical or nutraceutical dosage form.

Likewise as described in WO2008/049657 the inventive core/shell polymer compositions may be useful as binding agents and matrix formers for active ingredients included in retarded or sustained release oral dosage forms in order to minimize the effect of acceleration or deceleration of the active ingredient release by the influence of ethanol under in-vitro conditions.

EXAMPLES

Preparation of a Polymer Dispersion, According to the Invention

The polymer was prepared in a 1 liter round bottom flask, equipped with a lid, an anchor stirrer, a baffle, a reflux condenser, a feed pipe for nitrogen and a temperature probe to monitor the temperature inside the reactor. A water bath with a thermostat was used to control the reaction temperature.

653 g of deionized water, 13.2 g of sodium dodecylsulfate solution (15% in water; Disponil SDS 15) and 6.5 g of polysorbate 80 (TEGO SMO 80V) were charged into the flask. The reactor was flushed with nitrogen and the mixture was agitated with the stirrer and heated to a starting temperature of 82° C.

Two stable monomer emulsions were prepared for the core polymer and the shell polymer respectively. In sum 280.0 g of monomers were used, divided between the two flasks according to the desired ratio of core polymer to shell polymer. The monomer composition of each of the two emulsions was chosen according to the table of examples (see below). For each emulsion 3% by weight of deionized water, based on the weight of monomers, was used.

According to the invention, the core monomer emulsions included a cross-linking monomer (ethylene glycol dimethacrylate).

In the examples presented the shell monomer emulsions contained a chain transfer agent (thioglycolic acid 2-ethylhexyl ester).

The comparative example (example 1) was prepared without a core emulsion; the total 280.0 g of monomers were used to prepare the emulsion, which is in this case not intended to form a shell but a homogeneous particle.

As an example for Core Shell polymer composition of example 2—as in the table of examples—the core monomer emulsion was prepared with 83.7 g of n-butyl acrylate, 0.3 g of ethylene glycol dimethacrylate and 2.5 g of deionized water. The shell monomer emulsion was prepared from 58.6 g of 2-ethyl hexyl methacrylate, 58.6 methacrylic acid, 78.3 g of ethyl acrylate, 0.6 g thioglycolic acid 2-ethylhexyl ester (chain transfer agent) and 4.2 g of deionized water.

Two initiator solutions (for the preparation of the core polymer and the shell polymer, respectively) were prepared, by dissolving 0.12 mol % ammonium persulfate (with regard to the sum of used monomers of the core monomer emulsion and the shell monomer emulsion, respectively) in 5.0 g of deionized water.

When the temperature inside the reactor had reached 82° C., the initiator solution for the core polymer is added to the reactor. Two minutes later, the dosing of the core monomer emulsion was started at a dosing rate of 2 g/min. By adjusting the temperature of the water bath, the temperature inside the reactor was kept at 82° C. After all the core monomer emulsion was added, the temperature was kept for 10 minutes at 82° C., before the initiator solution for the shell was added to the reactor. 2 minutes later, the dosing of the shell monomer emulsion was started at a dosing rate of 2 g/min.

After all the shell monomer emulsion was added, the temperature was kept for another 30 minutes at 82° C., before the reactor content was allowed to cool down to 20° C. and was filtered through a 250 μm gaze.

Preparation of a Spraying Suspension 8.8 g of triethyl citrate, 210.0 g of micronized talc and 1057 g deionized water were charged into a vessel and homogenized for 15 minutes with an ULTRA TURRAX high-performance dispersing instrument.

350.0 g of the polymer dispersion (30% solids content) is stirred with a magnetic stirrer. After the talcum dispersion is slowly poured into to polymer dispersion, the stirring is continued for 60 minutes, before the mixture is filtered through a 240 μm gaze.

Coating Process

A MicroLab coater (Oystar Hüttlin) was used to prepare the coatings.

350 g of diprophylline pellets (diameter 0.7-1.0 mm, 20% active content) were charged into the MicroLab instrument and agitated with low air supply.

The fluid bed temperature was raised to 23-26° C. and the pellets were coated for 1.5 to 2.5 hour up to a polymer weight gain of 10.5 or 17.5% (additional weight due to polymer in coating with respect to initial pellet weight). The spray rate was raised slowly to a maximum of 2 g/min.

After the coating process, the pellets were agitated in the instrument for another 5 minutes for additional drying and curing. Then the coated pellets were allowed to cool down in the instrument with low air supply.

TABLE 1

Monomer compositions and Core/Shell ratios

| | core/shell ratio of polymer composition | monomer composition of core polymer | monomer composition of shell polymer |
|---|---|---|---|
| example 1 (comparative example) | 0/100 | no core | 39.9% EA<br>29.9 EHMA<br>29.9% MAA<br>0.3% TGEH |
| example 2 | 30/70 | 99.6% n-BA<br>0.4% EGDMA | 39.9% EA<br>29.9 EHMA<br>29.9% MAA<br>0.3% TGEH |
| example 3 | 50/50 | 99.6% n-BA<br>0.4% EGDMA | 39.9% EA<br>29.9 EHMA<br>29.9% MAA<br>0.3% TGEH |
| example 4 | 30/70 | 99.6% n-BuMA<br>0.4% EGDMA | 39.9% EA<br>29.9 EHMA<br>29.9% MAA<br>0.3% TGEH |
| example 5 | 50/50 | 99.6% n-BuMA<br>0.4% EGDMA | 39.9% EA<br>29.9 EHMA<br>29.9% MAA<br>0.3% TGEH |

TABLE 1-continued

Monomer compositions and Core/Shell ratios

| | core/shell ratio of polymer composition | monomer composition of core polymer | monomer composition of shell polymer |
|---|---|---|---|
| example 6 | 30/70 | 99.6% MMA<br>1.5% EGDMA | 39.9% EA<br>29.9 EHMA<br>29.9% MAA<br>0.3% TGEH |

MAA = methacrylic acid
EGDMA = ethylene glycol dimethacrylate
TGEH = thioglycolic acid 2-ethylhexyl ester
MA = methyl acrylate
EA = ethyl acrylate
n-BA = n-butyl acrylate
MMA = methyl methacrylate
n-BuMA = n-butyl methacrylate
EHMA = 2-ethyl hexyl methacrylate

TABLE 2

Properties of Core/Shell particles

| | rMS [nm] | Vz in THF [mL/g] | Tg [° C.] |
|---|---|---|---|
| example 1 (comp.) | 49 | n.d. | 49 |
| example 2 | 51 | 81.5 | 77 |
| example 3 | 51 | 92.4 | 68 |
| example 4 | 50 | 71.3 | n.d. |
| example 5 | 51 | n.d. | 32 |
| example 6 | 48 | 50.7 | 68 | n.d. = not determined

TABLE 3

Active Ingredient Release

| | Active Ingredient Release [%] | | |
|---|---|---|---|
| | after 120 min at pH 1.2 | after 120 min at pH 1.2 + 45 min at pH 6.8 | after 120 min at pH 1.2 with addition of 20% ethanol |
| example 1 (comp.) | 0.0 | 99.6 | 4.8 |
| example 2 | 0.4 | 100.0 | 2.4 |
| example 3 | 0.3 | 99.8 | 1.9 |
| example 4 | 0.1 | 99.7 | 1.2 |
| example 5 | 0.2 | 99.6 | 0.5 |
| example 6 | 0.3 | 99.7 | 2.6 |

Analytical Methods
Particle Size rMS [nm]

The particle size was determined by laser diffraction, using a Mastersizer 2000 (Malvern). The values are indicated as particle radius rMS [nm], which is half of the median of the volume based particle size distribution d(v, 50).

Viscosity number Vz [mL/g]

The viscosity number Vz is often used as a measure for the molecular weight. It was determined in accordance with DIN EN ISO 1628-1.

A process controlled viscosity measuring system (PVS, Lauda GmbH & Co. KG) with an Ubbelohde capillary (type Oc) was used.

The polymer was dissolved in THF, at a concentration of 0.5 g per 100 mL of solvent. The temperature of the measurement was 25° C.

Molecular Weight Mw [g/mol]

The molecular weight was determined by gel permeation chromatography (GPC). The molar mass calibration was based on poly(methyl methacrylate).

The conditions of the measurement were chosen according to the publication of Martina Adler et. al. (e-Polymers 2004, 055).

N,N-Dimethylacetamide with 6 g/L acetic acid, 3 g/L LiBr and 10 g/L $H_2O$ was used as a mobile phase, with a flow rate of 1.0 ml/min. A column set of 4 GRAM 10 μm columns (precolumn, 2×10.000 Å and 30 Å column—Polymer Standards Service, Mainz, Germany) was used as stationary phase.

Glass Transition Temperature Tg [° C.]

The glass transition temperature Tg was determined by DSC according to DIN EN ISO 11357. Typically between 10 and 12 mg sample, and a heating rate of 20 K/min was used; the temperature range was −40° C. to 140° C. The measurement is carried out under nitrogen atmosphere. The evaluation was based on the second heating cycle, and the indicated value is the mean value in the glass transition interval.

Minimum Film-Forming Temperature MFT [° C.]

The lowest temperature at which a polymer-dispersion will form a polymer film upon evaporation of the water is the minimum film-forming temperature (MFT). The MFT is characteristic of the dispersion and is—amongst others—influenced by the glass transition temperature and the particle size of the dispersed particles.

The minimum film-forming temperature has been determined according to DIN ISO 2115 by applying the dispersion with a doctor knife on a band heater at a defined temperature gradient. The MFT corresponds to the lowest temperature at which a crack-free film is formed and is slightly above the whitening point (which is the temperature at which the polymer still appears whitish because the film has not yet fully been formed).

Active Ingredient Release

The release properties were determined in a dissolution apparatus (USP 32 <711> dissolution; type 1: basket), at a rotation speed of 100 rpm, with 900 mL of dissolution medium. The temperature was 37° C.±0.5° C. The dissolution medium was 0.1 N hydrochloric acid (0.1 N HCl) for 2 hours; then a full exchange of the dissolution medium to pH 6.8 EP-buffer 4003200 (=phosphate buffered saline: 8.5 g NaCl, 1 g $KH_2PO_4$, 2 $K_2HPO_4$ in 1 L $H_2O$) was done. The amount of released API (diprophylline) was determined by UV-measurements.

The effect of ethanol was studied by replacing a part of the hydrochloric acid with ethanol. Measurements with 20% ethanol (by volume) were carried out.

The dissolution medium after the full exchange to pH 6.8 did not contain any ethanol (in all cases).

The invention claimed is:
1. A coating composition suitable for coating a pharmaceutical or nutraceutical dosage form comprising one or more pharmaceutical or nutraceutical active ingredients, from which coating composition the release of the pharmaceutical or nutraceutical active ingredient is not more than 10% under in-vitro conditions at pH 1.2 after 2 hours in medium according to USP with and without the addition of 20% (v/v) ethanol, the coating composition comprising:
at least 20% by weight of an enteric core/shell polymer composition derived from an emulsion polymerisation process, whereby a core of polymerized particles is first formed by polymerization of the monomers comprising the polymer or copolymer of the core and a shell is subsequently formed on the surface of the core particles by polymerization of the monomers comprising the polymer or copolymer of the shell, wherein the core of the core/shell polymer composition comprises a water-insoluble, cross-linked polymer or copolymer, and the shell of the core/shell polymer composition comprises an anionic polymer or copolymer, wherein the anionic polymer or copolymer consists essentially of:
(1) polymerized units of
   from 10 to 40% by weight of acrylic or methacrylic acid,
   from 10 to 50% by weight of ethyl acrylate,
   from 10 to 80% by weight of a C4- to C18-alkyl ester of acrylic or methacrylic acid, and
   optionally, from 0 to 20% by weight of methyl methacrylate; or
(2) polymerized units of
   from 40 to 60% by weight methacrylic acid and 60 to 40% by weight ethyl acrylate; or
(3) polymerized units of
   50% by weight methyl methacrylate and 50% by weight methacrylic acid; or
(4) polymerized units of
   from 10 to 30% by weight methyl methacrylate,
   from 50 to 70% by weight methyl acrylate, and
   from 5 to 15% by weight methacrylic acid.

2. The coating composition according to claim 1, further comprising up to 80% by weight of at least one pharmaceutical or nutraceutical excipient selected from the group consisting of an antioxidant, a brightener, a binding agent, a flavouring agent, a flow aid, a fragrance, a glidant, a penetration-promoting agent, a pigment, a plasticizer, a non-cross-linked polymer, a pore-forming agent, and a stabilizer.

3. The coating composition according to claim 1, which exists as a solid phase of an aqueous dispersion having a solid content of from 1 to 60% by weight.

4. The coating composition according to claim 1, which exists as a dry powder or a granulate.

5. The coating composition according to claim 1, further comprising one or more pharmaceutical or nutraceutical active ingredients.

6. The coating according to claim 1, wherein at least 20% by weight of an enteric core/shell polymer composition is derived from an emulsion polymerisation process whereby a core of polymerized particles is first formed by polymerization of the monomers for the polymer or copolymer of the core and a shell is subsequently formed on the surface of the core particles by polymerization of the monomers for the polymer or copolymer of the shell in the same reaction mixture.

7. The coating composition according to claim 1, wherein the water-insoluble, cross-linked polymer or copolymer comprises at least one selected from the group consisting of a crosslinked (meth)acrylate homopolymer and a crosslinked (meth)acrylate copolymer.

8. The coating composition according to claim 1, wherein the water-insoluble, cross-linked polymer or copolymer comprises at least one selected from the group consisting of a crosslinked polyvinyl homopolymer and a crosslinked polyvinyl copolymer.

9. The coating composition according to claim 1, wherein the water-insoluble, cross-linked polymer or copolymer is polymerized from n-butyl acrylate (n-BA) and a crosslinking monomer selected from the group consisting of (1) a monomer having more than one vinylic group, (2) a monomer having more than one allylic group, and (3) a monomer having at least one vinylic group and at least one allylic group.

10. The coating composition according to claim 1, wherein the water-insoluble, cross-linked polymer or copolymer is polymerized from methyl methacrylate (MMA) and a crosslinking monomer selected from the group consisting of (1) a monomer having more than one vinylic group, (2) a monomer having more than one allylic group, and (3) a monomer having at least one vinylic group and at least one allylic group.

11. The coating composition according to claim 1, wherein the water-insoluble, cross-linked polymer or copolymer is polymerized from n-butyl acrylate (n-BA) and a crosslinking ethyleneglycol-di-methacrylate (EGDMA) monomer.

12. The coating composition according to claim 1, wherein the water-insoluble, cross-linked polymer or copolymer is polymerized from methyl methacrylate (MMA) and a crosslinking ethyleneglycol-di-methacrylate (EGDMA) monomer.

13. The coating composition according to claim 1, wherein the water-insoluble, cross-linked polymer or copolymer is polymerized from 98-99.9% by weight of n-butyl acrylate (n-BA) and 0.1-2% by weight of a crosslinking ethyleneglycol-di-methacrylate (EGDMA) monomer.

14. The coating composition according to claim 1, wherein the water-insoluble, cross-linked polymer or copolymer is polymerized from n-butyl methacrylate (n-BuMA) and a crosslinking ethyleneglycol-di-methacrylate (EGDMA) monomer.

* * * * *